(12) United States Patent
Wu (10) Patent No.: US 8,765,726 B2
(45) Date of Patent: Jul. 1, 2014

(54) USE OF PYRIDONE DERIVATIVES IN THE PREVENTION OR TREATMENT OF TISSUE OR ORGAN TOXICITY INDUCED BY CYTOTOXIC AGENTS AND RADIATION

(75) Inventor: Jun Wu, Shanghai (CN)

(73) Assignee: Shanghai Genomics, Inc., Shanghai (CN)

( * ) Notice: Subject to any disclaimer, the term of this patent is extended or adjusted under 35 U.S.C. 154(b) by 629 days.

(21) Appl. No.: 11/958,353

(22) Filed: Dec. 17, 2007

(65) Prior Publication Data

US 2008/0161361 A1 Jul. 3, 2008

Related U.S. Application Data (63) Continuation-in-part of application No. PCT/CN2006/002504, filed on Sep. 25, 2006.

(60) Provisional application No. 60/804,914, filed on Jun. 15, 2006.

(51) Int. Cl.
  *A01N 43/00* (2006.01)
  *A61K 31/33* (2006.01)
  *A61K 31/44* (2006.01)
  *A61K 31/4418* (2006.01)

(52) U.S. Cl.
  CPC .................................. *A61K 31/4418* (2013.01)
  USPC .......................................... 514/183; 514/345

(58) Field of Classification Search
  CPC .................................................. A61K 31/4418
  USPC .................................................. 514/183, 345
  See application file for complete search history.

(56) References Cited

U.S. PATENT DOCUMENTS 6,114,353 A * 9/2000 Margolin ...................... 514/313

FOREIGN PATENT DOCUMENTS

CN  1701793    * 11/2005
CN  1701793 A    11/2005

OTHER PUBLICATIONS

Spond et. al., Pulmonary Pharmacology and Therapeutics (2003) 16:207-214.*
Chemocare.com (2005) pp. 1-4.*
Spond et. al. (Pulmonary Pharmacology and Therapeutics) 16:207-214).*
Chemocare.com (2005), pp. 1-4.*
Aliberti et. al. (CAS accession # 2005249316 corresponding to GIMT (2004) 58:449-461).*
Kong et. al. (Seminars in Oncology (2005) 32(Suppl. 3): S42-S54).*
Mehta (Seminars in Oncology (2004) 31 (Suppl. 18): 42-46).*
Raghu et. al. (Am. J. Respir. Crit. Care. Med. (1999) 159:1061-1069).*
Aliberti et. al. (CAS accession # 2005249316 corresponding to GIMT (2004) 58:449-46).*
Benton, et al. Modulation of articular chondrocyte activity by pirfenidone. Res Commun Mol Pathol Pharmacol. 2003;113-114:275-88.
Nicolaou, et al. Calicheamicin θ[1][1]: a rationally designed molecule with extremely potent and selective DNA cleaving properties and apoptosis inducing activity. Angew. Chem. Intl. Ed. Engl. 1994;33(2):183-186.
Spond, et al. Inhibition of experimental acute pulmonary inflammation by pirfenidone. Pulm Pharmacol Ther. 2003;16(4):207-14.
Xue, et al. A new antifibrotic tissue growth antagonist: pirfenidone. Chinese Journal of New Drugs. 2005;14(8): 1070-1072. (In Chinese with English abstract).

* cited by examiner

*Primary Examiner* — Marcos Sznaidman
(74) *Attorney, Agent, or Firm* — Wilson, Sonsini, Goodrich & Rosati (57) ABSTRACT

The present invention is directed to a novel use of pyridone derivatives such as pirfenidone for the prevention and treatment of damages to tissues or organs induced by various cytotoxic agents, such as chemotherapeutic agents, biologics, immunosuppressants and radiation. Such prophylactic and/or therapeutic effects of the pyridone derivatives make it possible to increase therapeutic dosages of the cytotoxic agent, thereby enhancing the therapeutic efficacy of the cytotoxic agent and radiation therapy.

2 Claims, 4 Drawing Sheets

Adriamycin-treated

Fig. 1A

Adriamycin+F351-treated

Fig. 1B

| Control | Bleomycin | Bleomycin+F351 | Bleomycin+dex |
| Fig. 2A | Fig. 2B | Fig. 2C | Fig. 2D |

| Control | Bleomycin | Bleomycin+F351 | Bleomycin+dex |
| Fig. 2E | Fig. 2F | Fig. 2G | Fig. 2H |

Control

Fig. 3A

CsA-treated

Fig. 3B

CsA+F35-treated

Fig. 3C

Adriamycin-treated

Fig. 4A

Adriamycin+F351-treated

USE OF PYRIDONE DERIVATIVES IN THE PREVENTION OR TREATMENT OF TISSUE OR ORGAN TOXICITY INDUCED BY CYTOTOXIC AGENTS AND RADIATION

CROSS REFERENCE TO RELATED APPLICATION

This application is a continuation-in-part of PCT Application PCT/CN2006/002504 filed on Sep. 25, 2006, which claims priority to U.S. Provisional Application No. 60/804,914, filed on Jun. 15, 2006, which applications are incorporated herein by reference in their entirety.

FIELD OF THE INVENTION

The present invention relates to the pharmaceutical field, and in particular, to a new use of pyridone derivatives in the prevention and treatment of tissue or organ toxicity induced by various cytotoxic agents, immunosuppressants, such as chemotherapeutic agents, biologics and radiation.

BACKGROUND OF THE INVENTION

General Background

A wide variety of cytotoxic agents or therapy, such as chemotherapy, immunosuppressive agents, biologics, radiotherapy and combined therapy thereof, are used in the treatment of cancer and many other diseases. However, when cancer cells are killed, normal cells are also damaged simultaneously when the treatment is used on human body. Typically, a series of toxic side effects occur, for example, the damage on important tissues and/or organs, such as heart, liver, kidney, lung, bone marrow, etc.

Radiation pneumonitis frequently appears after irradiation of the lung area during the treatment of lung cancer, breast cancer, and esophageal cancer. Radiation pneumonitis can lead to life threatening fibrotic lesion in the lung. Usually, the severity of pulmonary fibrosis is correlated with irradiation dosage. In addition, abdominal irradiation may induce hepatitis, enteritis, necrosis and fibrosis; whereas cavitas pelvis irradiation may induce rectitis and cystitis, of which the resulted mild symptom is mucosal dropsy and in the severe case is fibrosis.

The manifestations of pulmonary toxicity caused by drugs used in chemotherapy are interstitial pneumonia and pulmonary fibrosis. Drugs like Bleomycin, BCNU, MTX, Mitomycin, should be withdrawn once pulmonary toxicity appears, followed by further treatment with hormone, antibiotic, vitamin, etc. Drugs inducing liver toxicity include BCNU, CCNU, Ara-C, L-ASP, VP-16, 6-MP, high dose of MTX, CTX, DDP, DNR, Act-D, STZ, VCR, etc. Liver toxicity is divided into three types: (1) hepatocyte function defect and chemical hepatitis; (2) venous occlusion diseases; and (3) chronic liver fibrosis.

Drugs used in chemotherapy also cause renal toxicity. Most cytotoxic drugs, such as DDP, MTH, STZ, IFO, high dose of MTX, cause renal functional defect by damaging renal glomerulus, rather than renal tubule. Renal toxicity may occur immediately after drug administration or develops subsequently, after long-term medicine treatment or after withdrawal of the drugs.

Toxicity induced by combined chemotherapy and radiotherapy is divided into early stage and late stage, of which the late stage mainly involves damages of connective tissue within heart, kidney, lung, etc. Interstitial cardiac fibrosis may occur after three months following radiotherapy. For example, combined therapy of adriamycin and radiotherapy may increase associated cardiac toxicity. Drugs used in chemotherapy, such as bleomycin, adriamycin and mitomycin, may increase the incidence rate and severity of radiation pneumonitis and pulmonary fibrosis.

Injury of Organs Induced by Radiation

Radiotherapy is a common means for the treatment of malignant tumors. Radiation on pulmonary carcinoma, mammary adenocarcinoma, esophageal carcinoma, malignant lymphoma, or other thoracic malignant tumors will also damage normal pulmonary tissue in the irradiation filed, resulting in inflammation, which is termed as radiation-induced lung injuries, i.e. acute radiation pneumonitis.

Radiation pneumonitis is a major detrimental side effect during radiotherapy, including early change (radiation pneumonitis) and advanced change (radiation fibrosis). Everyone who has undergone a pulmonary irradiation will have such change. In most cases, such change is asymptomatic, but a change accompanied by infection will produce symptoms, which is called acute radiation pneumonitis. Asymptomatic inflammation will be gradually absorbed and disappear to form various degrees of pulmonary parenchyma fibrosis after completion of irradiation. Pulmonary fibrosis occurs within about 6 months after irradiation, and then gradually deteriorates to be worst within 1 year. Pathological changes of the acute phase of radiation pneumonitis occur mostly within 1 to 2 months after irradiation, but in some cases they are observed after a half year post radiotherapy. They manifest themselves as congestion, edema and cellular infiltration due to damage of pulmonary vessels (especially capillary vessel), decreased reproduction of type II alveolar cells, lymphangiectasis, and formation of hyaline membrane. The acute changes may spontaneously disappear, but they generally cause desmoplasia, fibrosis, and hyalinization of the lung. The chronic phase generally occurs after 9 months of irradiation, the pathologic of which is extensive fibrosis of pulmonary alveolus, contraction of lung, inner membrane thickening, stiffing, narrowing or obstruction of the lumen of blood capillary resulting in increased resistance force of pulmonary circulation and pulmonary artery hypertension. Pleura can also thicken as the result of inflammation and fibrosis. Epithelial anaplasia of the bronchiolar mucous lining and secondary pulmonary infection can promote radiation fibrosis.

Development of radiation pneumonitis is mostly correlate with the irradiation volume, while the other factors, such as dosage and separation, conditions of the individual, individual differences, and the presence of chronic lung diseases can also contribute. Use of anti-cancer agents, such as ADM, PYM, and VCR concurrently with radiation, as well as smoking, will also promote development of radiation pneumonitis.

The severity of lung injuries is closely correlated with the area of the lung irradiated, and the dose and rate of exposure. The pathological changes are exudative inflammation of the acute phase and, extensive pulmonary fibrosis of the chronic phase. The larger the dose received (more than 20 Gy), the more severe the radiation pneumonitis, eventually leading to the extensive pulmonary fibrosis. The occurrence of radiation pneumonitis greatly hampers the treatment of thoracic malignancies which are clinically common and progress rapidly, and thus negatively impacts patients' quality of life, or even threatens their lives. The incidence of radiation pneumonitis reportedly varies, generally in the range of about 8.25% to 58%.

Currently, there are not clinically available medicaments specifically for radiation-induced lung injuries. The common treatments include: i) corticoid therapy, to control inflammation; ii) anticoagulant therapy, to prevent small vascular embolism; iii) high concentration oxygen therapy, to alleviate hyoxemia; and iv) antibiotic therapy, to prevent secondary infection. The principle of administration is: i) prednisone or dexamethasone orally administered for general patients of radiation pneumonitis; ii) dexamethasone administered by intravenous infusion for severe patients; iii) antibiotics concurrently administered for patients who have concomitant pulmonary infection. However, the effect of hormone treatment is still in question, because some investigations have showed that hormone treatment has no effect on radiation-induced lung injuries.

It is undoubted that radiotherapy plays an important role in the treatment of malignancies, however, its side effects of irradiative responses and injuries are also noteworthy. High dose of irradiation damages tumor cells as well as normal cells, causing detrimental responses in the patients. If the irradiation dose is not limited, it will kill normal cells when it kills the tumor. Therefore, radiation therapy can only kill tumor cells to the most extent where it is tolerated by normal tissues. In the situation of a radio-sensitive tumor, a tumor-killing dose will not damage normal tissues around the tumor, and hence the radiation therapy can cure the tumor. While for a tumor whose fatal irradiation dose can also kill or damage the surrounding normal tissue, normal tissue will be greatly damaged at the same time with tumor cells. Therefore, it is necessary to utilize suitable treatment modalities to increase the ratio of the doses received by tumor versus normal tissue so as to cure the tumor but not overly influence the normal tissue. In addition, there is an earnest need in the art to develop a method with increased irradiation dose and decreased radiation-induced injuries.

In summary, cytotoxic therapy such as chemotherapy and radiotherapy often causes acute tissue injury and fibrosis, thus limiting the efficacy and safety of the treatment. Currently there is no effective prophylactic or treatment regimen available for such side effects during the treatment using a cytotoxic therapy.

SUMMARY OF THE INVENTION

The present invention provides innovative compositions, kits and methods for preventing, alleviating or treating of damages to tissues or organs induced by various cytotoxic agents, immunosuppressants or therapy, such as chemotherapeutic agents, biologics and radiation.

In one aspect of the invention, the present invention provides a method for preventing, treating or reducing damage to a tissue or organ of a mammal who has been, is being, or will be treated with a cytotoxic agent, an immunosuppressant, and/or radiation, comprising: administering to the mammal a therapeutically effective amount of a compound of Formula I or a pharmaceutically acceptable salt thereof, (I)

wherein $R_1$ is methyl, ethyl or trifluoromethyl at position 3, 4, 5 or 6; and $R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent.

In a preferred embodiment, the compound is pirfenidone.

In another preferred embodiment, the compound is 5-methyl-1-(4-hydroxylphenyl)-2-(1H)-pyridone, which is called F351.

According to the method, the cytotoxic agent may be a chemotherapeutic agent such as alkylating agents, antimetabolites, and hormonal agents. The biologic may be a therapeutic antibody or cytokine. The radiation may be ionizing radiation.

The mammal may be a rodent such as a mouse or rat, but preferably a human, more preferably a human patient having cancer, tumor or in need of a tissue or organ transplant.

In one embodiment, the compound of Formula I is administered prior to the treatment of the cytotoxic agent, immunosuppressant, or radiation.

In another embodiment, the compound of Formula I is administered on the same day when the mammal is treated with the cytotoxic agent, immunosuppressant, or radiation.

In yet another embodiment, the compound of Formula I is administered after the mammal is treated with the cytotoxic agent, immunosuppressant, or radiation.

In another aspect of the invention, a method is provided for allowing increased therapeutic irradiation dosage of a radiotherapy or of a chemotherapy of a mammal, comprising: administering to the mammal a compound of Formula I or a pharmaceutically acceptable salt thereof,

(I)

wherein, $R_1$ is methyl, ethyl or trifluoromethyl at position 3, 4, 5 or 6; and $R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent.

In a preferred embodiment, the radiation or chemo therapy is for the treatment of cancer or tumor, such as lung cancer, breast cancer, esophageal carcinoma, malignant lymphoma, and other thoracic malignant tumors of the mammal.

In a preferred embodiment, the compound is pirfenidone.

In yet another aspect, the present invention provides a method for preventing lung injury induced by radiation therapy or chemotherapy of a mammal, comprising the steps of: before a radiotherapy or a chemotherapy, administering to said mammal a prophylactically effective amount of a compound of Formula I or a pharmaceutically acceptable salt thereof, (I)

wherein $R_1$ is methyl, ethyl or trifluoromethyl at position 3, 4, 5 or 6; and $R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent.

In a preferred embodiment, the radiation or chemo therapy is for the treatment of cancer or tumor, such as lung cancer, breast cancer, esophageal carcinoma, malignant lymphoma, and other thoracic malignant tumors of the mammal.

In yet another aspect, the present invention provides a method for increasing the therapeutic irradiation dosage or the therapeutic dosage of chemotherapy for a mammal, comprising the steps of: (a) administering to said mammal in need of a radiotherapy or a chemotherapy a compound of formula I or a pharmaceutically acceptable salt thereof, (I)

wherein $R_1$ is methyl, ethyl or trifluoromethyl at position 3, 4, 5 or 6; and $R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent, wherein, there is an original therapeutic irradiation dose or chemotherapeutic dose set to be $D_0$ for said mammal; and (b) subjecting said mammal to a radiotherapy at an irradiation dose or chemotherapeutic dose of $D_1$, wherein $D_1 > D_0$.

In a preferred embodiment, said irradiation dose or chemotherapeutic dose $D_1$ and $D_0$ fit the following equation:

$$(D_1-D_0)/D_0 \geq 90\%.$$

In a preferred embodiment, the compound is Pirfenidone.

In a preferred embodiment, the radiation or chemo therapy is for the treatment of cancer or tumor, such as lung cancer, breast cancer, esophageal carcinoma, malignant lymphoma, and other thoracic malignant tumors of the mammal.

In a preferred embodiment, the compound of formula I is administered at about 1 to 10 days (such as 2, 3, 4, 5, 6, 7, 8, or 9 days) before the radiotherapy or chemotherapy.

In an embodiment, the dose of the compound of formula I administered is 0.1-1000 mg/kg, 0.5-500 mg/kg, 1-200 mg/kg, or 10-100 mg/kg body weight per day.

DETAILED DESCRIPTION OF THE INVENTION

The present invention provides innovative compositions, kits and methods for preventing, alleviating or treating of damages to tissues or organs induced by various cytotoxic agents, such as chemotherapeutic agents, biologics, immunosuppressants and radiation. Inventors found that pyridone derivatives provided in the present invention are able to prevent or reduce injuries to a mammal who is treated with chemotherapy, an immunosuppressant or radiation therapy. Thus, such prophylactic and/or therapeutic effects of the pyridone derivatives make it possible to increase therapeutic dosages of the cytotoxic agent, thereby enhancing the therapeutic efficacy of the cytotoxic agent.

As exemplified in the Example section, animals treated with chemotherapeutic agents (e.g., bleomycin and Adriamycin (i.e., doxorubicin), an immunosuppressant (e.g., cyclosporine) and radiation suffered from extensive damages in the kidney and lung. In contrast, when treated with the pyridone derivatives (e.g., pirfenidone and F351), such damages to the animal were significantly reduced, marked by reduced mortality rates, and reduced fibrosis in the kidney and lung. Compared with a conventional anti-inflammatory agent, dexamethasone, the pyridone derivatives provided in the present invention are not only safer but also efficacious in protecting the animals from the cytotoxic side effects of the drugs and radiation. Thus, the present inventions are particularly useful in treatment of various diseases involving the use of cytotoxic drugs or radiation.

In one aspect of the invention, the present invention provides a method for preventing, treating or reducing damage to a tissue or organ of a mammal who has been, is being, or will be treated with a cytotoxic agent, an immunosuppressant, and/or radiation, comprising: administering to the mammal a therapeutically effective amount of a compound of Formula I or a pharmaceutically acceptable salt thereof, (I)

wherein $R_1$ is methyl, ethyl or trifluoromethyl at position 3, 4, 5 or 6; and $R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent.

In a preferred embodiment, the compound is pirfenidone.

In another preferred embodiment, the compound is 5-methyl-1-(4-hydroxylphenyl)-2-(1H)-pyridone, which is called F351.

According to the method, the cytotoxic agent may be a chemotherapeutic agent.

As used herein the term "chemotherapeutic agent" or "chemotherapeutic" (or "chemotherapy", in the case of treatment with a chemotherapeutic agent) is meant to encompass any non-proteinaceous (i.e., non-peptidic) chemical compound useful in the treatment of cancer, tumors, or other diseases. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phi1I, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g. paclitaxel (TAXOL™, Bristol Meyers Squibb Oncology, Princeton, N.J.) and docetaxel (TAXOTERE™., Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylomithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LYI 17018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femarar™), and anastrozole (Arimidex™); and anti-androgens such as flutamide, nilutamide, bicalutamide, leuprolide, and goserelin; and pharmaceutically acceptable salts, acids or derivatives of any of the above.

The cytotoxic agent may also be a tyrosine kinase inhibitor such as ZD 1839 (Iressa™ of AstraZeneca K.K.); IMC-C225 or cetuximab (Erbitux™); imatinib mesylate (GLEEVEC™, formerly STI-571); and Sorafenib (Nexavar™).

The biologic may be a therapeutic antibody such as trastuzumab (HERCEPTIN™); Rituximab (RITUXAN™); alemtuzumab (CAMPATH™); and Gemtuzumab zogamicin (MYLOTARG™).

The biologic may also be a cytokine such as the interleukins and tumor-necrotic factors (TNFs).

Examples of the immunosuppressant include, but are not limited to, Cyclosporins (Neoral, Sandimmune, SangCya); Azathioprines (Imuran); corticosteroids such as prednisolone (Deltasone, Orasone); basiliximab (Simulect); daclizumab (Zenapax); muromonab CD3 (Orthoclone OKT3); tacrolimus (Prograf); Glatiramer acetate (Copaxone); Mycophenolate (CellCept) and Sirolimus (Rapamune).

The radiation may be ionizing radiation.

The mammal may be a rodent such as a mouse or rat, but preferably a human, more preferably a human patient having cancer, tumor or in need of a tissue or organ transplant.

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neurons, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

In one embodiment, the compound of formula I is administered prior to the treatment of the cytotoxic agent, immunosuppressant, or radiation.

As used herein, the terms "the compound of the present invention", "(a) pyridone derivative(s)", "a compound of formula I", which are used interchangeably, refer to a compound having structural formula I or a pharmaceutical acceptable salt thereof, wherein $R_1$ is methyl, ethyl or trifluoromethyl at position 3, 4, 5 or 6; and $R_2$ is hydroxyl, sulfydryl, $C_{1-6}$ alkoxyl such as methoxyl, and ethoxyl, or a $C_{1-6}$ alkylthio group such as a methylthio group or an ethylthio group at position 2, 3 or 4; or, $R_2$ is absent.

In a preferred embodiment, $R_1$ is methyl, and $R_2$ is absent. In a further preferred embodiment, R is methyl, and $R_2$ is hydroxyl. More preferably, $R_1$ is methyl at position 5, and $R_2$ is hydroxyl at position 4.

A particularly preferred compound is Pirfenidone.

Another particularly preferred compound is 5-methyl-1-(4-hydroxylphenyl)-2-(1H)-pyridone, which is called F351 having the structure shown below.

The compounds of the present invention may also be in the form of a salt formed with a pharmaceutically or physiologically acceptable acid or base. Such salts include (but not limited to) the salts formed with an inorganic acid selected from the group consisting of hydrochloric acid, sulphuric acid, nitric acid and phosphoric acid or an organic acid selected from the group consisting of acetic acid, ethanedioic acid, butanedioic acid, tartaric acid, methane sulfonic acid and maleic acid. Also, the salts include those formed with an alkali metal or an alkaline earth metal such as sodium, potassium, calcium or magnesium, and those in the form of so-called "pro-drugs", which can be transformed into active ingredients in vivo, including but not limited to esters and carbamates.

The present invention also encompasses a pharmaceutical composition and a therapeutic method. The said method comprises a step of administration of a pharmaceutically effective amount of a compound of formula I to a mammal.

When the compound of the present invention is used in the above-mentioned application, it can be mixed with one or more pharmaceutically acceptable carriers or excipients such as solvents, diluents, etc., and can be orally administered in a dosage form selected from: tablets, pellets, capsules, dispensable powder, particles or suspension (containing, e.g. about 0.05-5% suspending agent), syrup (containing, e.g. about 10-50% saccharide), and elixirs (containing, about 20-50% ethanol), topically administered in the form of ointment, gel, medicated bandage or patch, etc, or administered parenterally in the form of a sterile injectable solution or suspension (containing about 0.05-5% suspending agent in an isotonic medium). For example, a pharmaceutical preparation of the invention may contain, on a weight basis, about 0.01-99%, preferably about 0.1%-90% of active ingredients mixed with one or more carriers.

The effective dose of the active ingredient may vary with the compound used, the administration mode and the severity of the disease to be treated. However, typically, a desirable result can be obtained when the compound of the present invention is administered at about 0.25-1000 mg/kg body weight per day. More preferably, the amount is separated into 2-4 doses per day, or is delivered via a sustained-release form. For most of the large mammals, the daily dose is about 1-100 mg/kg, more preferably about 2-80 mg/kg. The dosage form suitable for oral administration comprises about 0.25-500 mg of the active compound homogeneously mixed in a solid or liquid pharmaceutically acceptable carrier. This dosing regime may be adjusted to obtain the best therapeutic response. For example, depending on the urgency of the condition to be treated, several separate doses may be administered daily, or the dosage may be reduced in proportion.

The active compounds may be administered orally, intravenously, intramuscularly or subcutaneously. Solid carriers include starch, lactin, dicalcium phosphate, microcrystalline cellulose, sucrose and white bole, and liquid carriers include sterile water, polyethylene glycol, nonionic surfactant and edible oil (e.g. corn oil, peanut oil and sesame oil), as long as these carriers are compatible with the active ingredients and the desired mode of administration. Advantageously, the adjuvants commonly used in the production of a pharmaceutical composition, for example, a flavoring agent, colorant, preservative and antioxidant such as vitamin E, vitamin C, BHT and BHA, are also included.

To ease the production and the administration, the pharmaceutical composition is preferably a solid one, especially in the form of tablets and capsules filled with solid or liquid. Oral administration of the compound is preferred.

The active compounds may be administered parenterally or intraperitoneally. The active compounds (as free bases or pharmaceutically acceptable salts) may be formulated into aqueous solutions or suspensions mixed with surfactant (e.g. hydroxypropyl cellulose, polyvinyl pyrrolidone) as desired. Dispersions can also be prepared by mixing the active compounds in glycerin, liquid, polyethylene glycol and/or oil. For the storage and usage under normal condition, the preparations may contain preservatives to prevent the growth of microorganisms.

The injectable forms include sterile aqueous solutions and dispersions and sterile powder (freshly formulated into sterile injection solutions or dispersions before use). Whatever, the formulations should be sterile, and have sufficient fluidity to allow the discharge from the injection devices such as a syringe. The formulations should be stable under the condition of production and storage, and capable of preventing contamination by microorganisms (such as bacteria and fungi). The carrier may be a solvent or a dispersant, including, for example, water, alcohols (such as glycerin, propylene glycol and liquid polyethylene glycol), the mixture thereof, and plant oil.

Additionally, the compound of the present invention may be used in combination with one or more additional agents such as α-interferon, β-interferon, γ-interferon, cortical hormone and methotrexate.

When used for prophylaxis (or treatment) of acute lung injuries, the pharmaceutical composition of the invention comprises a pharmaceutically acceptable vehicle and a compound of formula I (e.g. Pirfenidone), wherein the content of the compound of formula I is in the range of 0.01% to 99.99% by weight, preferably 0.1% to 95% by weight, more preferably 0.5% to 90% by weight. Additionally, the pharmaceutical composition may comprises an agent selected from the group consisting of: a protease inhibitor, for example, Sivelestat Sodium, anti-inflammatory agents, for example, Ibuprofen, interferons and other non-steroid anti-inflammatory drugs, phosphodiesterase inhibitor, for example, Pentoxifylline, cytoprotector Amifostine, antioxidants N-acetylcysteine, anti-endotoxin monoclonal antibody against inflammatory cells, the medium thereof, and some pathogenic factors, IL-1 receptor antigonist (IL-1 ra), TGF and its receptor antigonist, TGF α and its receptor antigonist, and EGF/PDGF and its receptor antigonist. It can also comprise a herb or its extract selected from the following: salvia, astragalus, turtle shell or the mixture thereof.

The dosage form of the present pharmaceutical composition is not specifically limited. It may take the form of solid, semi-solid or liquid. The pharmaceutical formulation according to the present invention may be administered intravenously, subcutaneously, or via other suitable administration routes. Oral administration is preferred to give the desired effect. Also preferred is parenteral administration, such as intravenous injection, which can reduce the delay before the medicament takes effect in vivo.

The subject which can be treated with the present pharmaceutical composition and by the method is mammals, in particular human beings.

Although the effective therapeutic amounts of Pirfenidone will vary with the ages and the conditions of the patient to be treated, the prophylactic amount is generally from about 0.1 to 500 mg/kg, preferably from 0.1 to 200 mg/kg, more preferably from 0.5 to 100 mg/kg, still more preferably from 1 to 80 mg/kg. The frequency of administration may be once or more than once a day.

The present invention provides a method for preventing radiation-induced lung injuries, comprising administering a prophylactically effective amount of Pirfenidone to a patient in need of a radiation therapy before the radiation therapy.

The present invention also provides a method to allow an increased therapeutic irradiation dosage, comprising administering a prophylactically effective amount of Pirfenidone to a patient to be treated at an original irradiation dose of $D_0$, and then subjecting the patient to a radiation therapy at a irradiation dose of $D_1$, wherein $D_1 > D_0$, preferably $D_1$ is higher than $D_0$ by 20%, more preferably by 50%.

As used herein, the term "prophylactically effective amount" refers to an administration amount which is capable of preventing the radiation-induced lung injuries. Typically, this prophylactically effective amount is from 1 to 50 mg/kg body weight/day.

According to the present invention, Pirfenidone can be used alone or in combination with pro-drugs.

The main advantages of the present invention lie in:

(i) Pirfenidone has remarkable prophylactic effect on radiation-induced lung injuries with high safety and few toxic side-effects;

(ii) Pirfenidone treatment allows a significantly increased therapeutic irradiation dose.

The present invention will be further illustrated with the following examples. It should be understood that, these examples are exemplary only and are not intended to limit the scope of the present invention. The experimental methods in the following examples not indicating the specific experimental conditions are typically carried out under the conventional conditions, or following the manufacture's instructions.

EXAMPLES

Example 1

I. The Effects of Pirfenidone on Radiation-Induced Lung Injuries (a) Irradiation Method Irradiation source: Varian 600C linear accelerator, 6MV X ray Irradiation method: The mice, six per row, were each detained in an organic-glass cage. The cage was lid with a 1.5 cm thick organic glass plate to compensate the buildup effect. The source-to-skin distance was 100 cm, the irradiation field was 2.5×18 cm. The animal's head and abdomen were sheltered by the lead baffle of the collimator, and thus only the chest was exposed to the irradiation. The single dose of irradiation is 1200 cGy. A sealed transfer box equipped with an air filtering device should be used to transfer the animals from or back to the animal house.

Animals: 10-week old BALB/C mice (b) Grouping of Animals:

Control Model group (60 mice): The mice were irradiated but not treated with the compound.

Prophylaxis group (60 mice): The medication at a predetermined dose was started 2 days before the irradiation. The irradiation method and the dosage were the same as in the control group. Pirfenidone was administered by gauvage (200 mg/kg, dissolved in 0.5% CMC-Na and administrated at the volume of 0.1 ml/10 g) once a day for 3 months.

Treatment group (60 mice): The medication was started at day 0 of the irradiation. The irradiation method and dosage were the same as in the control group. Pirfenidone was administered by gauvage (200 mg/kg, dissolved in 0.5% CMC-Na and administrated at the volume of 0.1 ml/10 g) once a day for 3 months.

Blank control group (60 mice): The mice were not irradiated, and were only administered by gauvage with 0.5% CMC-Na once a day for 3 months.

The mice of each group were observed once a day after irradiation to examine the mortality. The cytometry and cell sorting of the lavage, collagen content measurement (hydroxyproline), pathomorphological observation were conducted periodically after medicament treatment.

Cytometry of the bronchial alveolar lavage liquid: the right lung was perfused with normal saline. 1.5-2.0 ml lavage liquid was collected into an Ependoff tube by gentle suction. The content of the inflammatory cells was counted manually by use of a haemocytometer immediately after collection of the bronchial alveolar lavage liquid.

Measurement of the hydroxyproline content: The measurement was performed with isolated lung tissue by following the instruction in the hydroxyproline kit.

Histopathologic examination: The isolated lung tissue was fixed in formaldehyde solution, pafarrin-imbeded after dehydration, and then subjected to HE staining and Masson trichrome staining. Evaluation criteria: Radiation-induced lung injuries was evaluated according to the standard semi-quantitative scoring of the Ashcroft interstitial pulmonary fibrosis.

II. Results

Figure 1A:
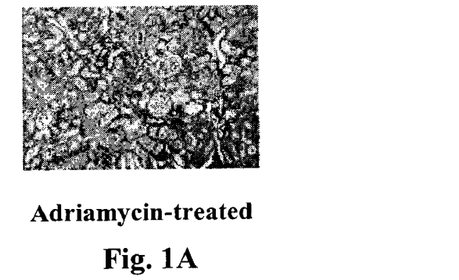
FIG. 1 shows effects of F351 on reduction of renal fibrosis induced by Adriamycin via pathological examination. Panel A: Adriamycin-treated; and Panel B: Adriamycin+F351-treated.
Figure 1B:
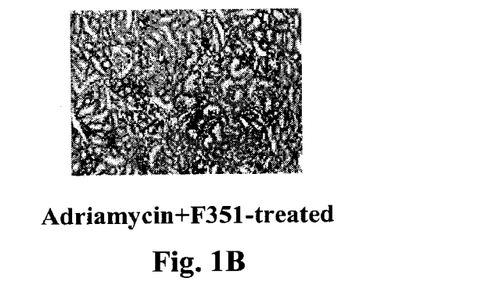
Figure 2A:
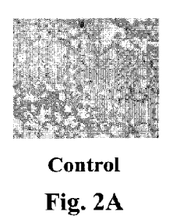
FIG. 2 shows effects of F351 on reduction of lung fibrosis induced by bleomycin via pathological examination with HE staining (panels A-D, A: Control; B: Bleomycin-treated; C: Bleomycin+F351-treated; D: Bleomycin+dexamethasone-treated); and Masson staining (panels E-H, E: Control; F: Bleomycin-treated; G: Bleomycin+F351-treated; H: Bleomycin+dexamethasone-treated).
Figure 2B:
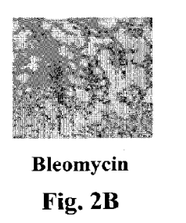
Figure 2C:
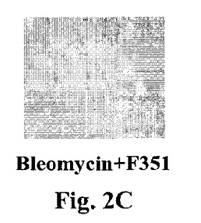
Figure 2D:
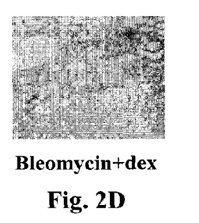
Figure 2E:
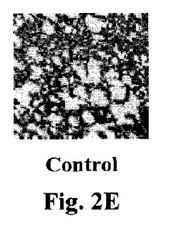
Figure 2F:
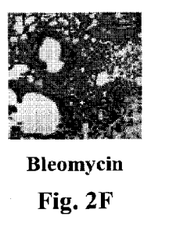
Figure 2G:
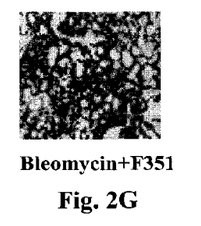
Figure 2H:
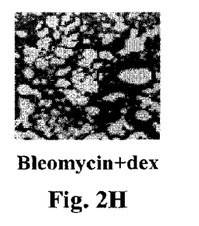

The experiments showed that prophylactic and therapeutic administration of Pirfenidone can both reduce the amount of inflammatory cells in the bronchial alveolar lavage liquid, which suggested that Pirfenidone has an inhibitory effect on pulmonary inflammation response induced by radioactive irradiation. The prophylactic administration showed more significant effect than the therapeutic administration (FIG. 1 and Table 1).

TABLE 1

CELL COUNT OF BRONCHIAL ALVEOLAR LAVAGE LIQUID

| | Month 2 | Month 3 | Month 4 | Month 5 | Month 6 |
|---|---|---|---|---|---|
| Blank control | 1.09 | 0.31 | 0.75 | 2.02 | 0.87 |
| Model control | 5.16 | 4.72 | 18.51 | 60.61 | 46.21 |
| Treatment group | 5.78 | 1.04 | 8.04 | 45.55 | 39.29 |
| Prophylaxis group | 2.27 | 2.03 | 4.5 | 27.7 | 15 |

The experiments also showed that Pirfenidone could obviously reduce the content of hydroxyproline (i.e. the amount of collagen synthesis) in lung tissue, which suggested that Pirfenidone has an inhibitory effect on fibrosis lesion induced by the radiation. Surprisingly, the prophylactic administration showed more significant effect than the therapeutic administration. The difference was particularly significant in Month 5 and Month 6 (FIG. 2 and Table 2). This suggests that prophylactic administration is more beneficial.

TABLE 2

MEASUREMENT OF HYDROXYPROLINE IN THE WHOLE LUNG

| | Month 1 | Month 2 | Month 3 | Month 4 | Month 5 | Month 6 |
|---|---|---|---|---|---|---|
| Blank control | 40.75 | 50.81 | 54.77 | 52.51 | 55.67 | 52.74 |
| Model control | 40.29 | 46.87 | 54.8 | 64 | 69.97 | 79.51 |
| Treatment group | 36.11 | 46.36 | 52.13 | 60.38 | 67.92 | 68.24 |
| Prophylaxis group | 43.85 | 43.81 | 50.46 | 56.98 | 58.1 | 58.15 |

Example 2

I. Pirfenidone can Increase the Tolerance to the Therapeutic Irradiation Dosage (a) Method: the Same as Described in Example 1.

Prophylaxis group (60 mice): The medication was started 2 days before the irradiation. The mice were divided into two groups. The animals were administered by gauvage with Pirfenidone (200 mg/kg, dissolved in 0.5% CMC-Na and administrated at the volume of 0.1 ml/10 g) once a day for 3 months.

Each group consisted of 60 mice. The mice of each group were observed once a day after irradiation to examine the dyspnea and mortality. The lung weighing, cytometry and cell sorting of the bronchial alveolar lavage liquid, collagen content measurement (hydroxyproline), measurement of cytokines (ACE, TGF-$\beta$, TGF-$\alpha$ etc) in the plasma, and pathomorphological observation were conducted periodically after the medicament treatment.

The results indicated:

When Pirfenidone was administered prophylactically, the cell count in the bronchial alveolar lavage liquid was lower than that of the control group. This suggests that administration of Pirfenidone before irradiation allow an increased therapeutic irradiation dose.

Example 3

Twelve healthy subjects were administered with Pirfenidone capsule at the dose of 400 mg, once a day or three times a day. The medication continued for 5 days. The blood level of the medicine was measured every day. The results indicated that blood stasis was achieved at day 3 of the continuous administration at 400 mg. This suggests that prophylactic administration of Pirfenidone (for example, 2 days before the irradiation) can achieve the blood stasis in vivo which may improve the therapeutic efficacy.

Example 4

I. Preparation of the Pharmaceutical Composition Comprising Pirfenidone (a) Injectable Formulation Table 3 below lists the ingredients of an exemplary formulation.

TABLE 3

| | |
|---|---|
| Pirfenidone/F351 | 20-100 mg |
| Sodium chloride | 1-5 mg |
| Water for Injection | to the volume of 10 ml |

Pirfenidone and sodium chloride were weighted according to the above formulation, and were formulated into a solution. The solution was then filled into 10 ml vials, sterilized and packaged.

(b) Oral Formulation: Capsules

Table 4 below lists the ingredients of an exemplary oral formulation in a form of capsule.

TABLE 4

| | |
|---|---|
| Pirfenidone/F351 | 50-500 mg |
| Hydroxypropylmethylcellulose | 2-10 mg |
| Starch | 50-100 mg |
| Lactose | 2-10 mg |

The above excipients for 1000 capsules were weighed, grinded, sieved and mixed to be homogenous. Then, the mixture was added into Pirfenidone in the way of incremental addition. The mixture was grinded to be homogenous, and then sieved through 80 mesh before filled into capsule.

(c) Oral Formulation: Sustained-Release Tablets

Table 5 below lists the ingredients of an exemplary oral formulation in a form of sustained-release tablet.

TABLE 5

| | |
|---|---|
| Pirfenidone/F351 | 50-500 mg |
| Hydroxypropylmethylcellulose | 20-100 mg |
| Sodium alginate | 50-100 mg |
| Lactose | 100-200 mg |
| Microcrystalline cellulose | 50-200 mg |
| Magnesium stearate | 2-10 mg |

Pirfenidone, lactose, hydroxypropylmethylcellulose and sodium alginate were respectively weighted according to the formulation indicated above (for 1000 capsules), grinded to fine powder, sieved through 80 mesh and admixed. Then, the mixture was mixed uniformly with microcrystalline cellulose, and was wetted with water, screened through a 16-18 mesh sieve, dried at 60° C., granuled. Magnesium stearate was then added, and the mixture was pressed into tablets.

(d) Oral Formulation Also Containing Herb Medicine

Table 6 below lists the ingredients of an exemplary oral formulation in a form of capsule.

TABLE 6

| | |
|---|---|
| Pirfenidone/F351 | 50-500 mg |
| *Salvia* (Dan Shen root) extract | 50 mg |
| Hydroxypropylmethylcellulose | 2-10 mg |
| Starch | 50-100 mg |
| Lactose | 2-10 mg |

The above excipients for 1000 capsules were weighed, grinded, sieved, and mixed to homogeneity. Then, the mixture was added into Pirfenidone in the way of incremental addition. The mixture was grinded thoroughly to be homogeneous, and then sieved through 80 mesh before filled into capsule.

Example 5

I. Synthesis of a Pirfenidone Analog

The analog was obtained through the following reaction, wherein $R_1$ in formula I is methyl at position 4, $R_2$ is hydroxymethyl at position 4:

4-methylpyridin-2(1H)-one was dissolved in dichloromethane, to which pyridine in a catalytic amount was added. The temperature was controlled between 0 to 5° C.

1-bromo-4-methoxybenzene was slowly dropped into this mixture and allowed to react at room temperature for 2 hours. The reaction mixture was poured into ice water, extracted twice with dichloromethane, and the organic layer was collected. The collected organic layer was washed with saturated saline solution, dried over sodium sulfate, and then concentrated to give a crude product. The crude product was subject to column chromatography to give the final product.

Example 6

I. Effect of 5-methylpyridin-1(4-hydroxyphenyl)-2-(1H)-one on Radiation-Induced Lung Injuries The experiments in Example 1 are repeated, except that 5-methylpyridin-1(4-hydroxyphenyl)-2-(1H)-one (F351) rather than Pirfenidone is used, with twenty mice in each group.

The experiments should show that prophylactic and therapeutic administration of compound F351 can both reduce the amount of inflammatory cells in the bronchial alveolar lavage liquid. And, the prophylactic administration may be more effective than the therapeutic administration.

Discussion

Lung injuries is a common problem during radiotherapy of thoracic tumors, which include two phases, early and late phases of radiation-induced lung injuries. The early-phase lung injuries (radiation pneumonitis) generally occurs during the course of irradiation, leading to severe consequence including interruption of the irradiation course and thus influencing the therapeutic effect, or even leading to death of patients.

Pulmonary infection can also deteriorate fibrosis of the lung. Late phase of the radiation-induced lung-injuries primarily depends on prophylaxis. There is not currently available medicament specifically for the treatment of radiation-induced lung-injuries, and the prophylactic medicament for this disease has not been reported yet.

Once the pulmonary fibrosis has occurred, the treatment will be a complex and long-term course. Though Pirfenidone has excellent clinically therapeutic effect on radiation-induced lung injuries, it does not guarantee that the patient can be completely cured without any sequelae. Consequently, prevention before the onset is more practically important than treatment after onset of the disease. Pirfenidone, a small compound, has the effect of inhibiting tissue fibrosis, improving pulmonary function, anti-inflammation, and anti-fibrosis. When being administered before the formation of pulmonary fibrosis, Pirfenidone can inhibit collagen synthesis, prevent fibroblast proliferation, and down-regulate many cytokines, thereby preventing development of radiation pneumonitis and radiation pulmonary fibrosis.

Radiation-induced lung injuries during radiotherapy can hardly be avoided. Administration of Pirfenidone compounds before radiotherapy can, on one hand, kill tumorous tissues, and on the other hand, provide the best prevention against radiation-induced lung injuries, and hence improve life quality of the patients, thereby greatly enhancing the therapeutic effect on tumors. Therefore, it has significant theoretic and clinical values.

Example 7

I. Treatment of Adriamycin-Induced Renal Toxicity Using F351

Methods:

20 male Wistar rats (with body weight 180-220 g) were randomly divided into three groups with 4 rats in control group, 8 rats in Adriamycin-treated group, and 8 rats in Adriamycin+F351-treated group. All the animals (except for those in control group) were injected with 7.5 mg/kg adriamycin by tail vein injection on day 1 of the study. Animals in Adriamycin+F351-treated group were administrated by gauvage with 250 mg/kg F351 per day for 12 weeks starting on day 1 of the study. Animals in the control group were injected with PBS, instead. The study lasted for 12 weeks.

Observation:

Rat urine was collected 24 hours before the end of the study and amount of urine proteins was determined. Renal tissues were also collected for pathology examination.

Results:

As shown in Table 7, treatment of F351 reduced amount of urine proteins significantly. We also observed that treatment of F351 reduced the degree of kidney fibrosis by pathology examination. As shown in FIG. 1, animals in Adriamycin-treated group showed glomerular intumescence, increased mesangial cell proliferation and mesangial matrix, focal segmental sclerosis, hyperplasia of focal fibrous tissue in tubule, and increased collagen deposition (Green color in masson staining indicated collagen deposition). Animals in F351-treated group showed slight glomerular intumescence, normal mesangial cell proliferation, slight hyperplasia of focal fibrous tissue, decreased inflammatory cell infiltration, and reduced collagen deposition.

TABLE 7

EFFECT OF F351 ON REDUCTION OF AMOUNT OF URINE PROTEINS

| Group | Amount of Urine Proteins (mg/24 hrs, x ± s) |
|---|---|
| Control | 9.33 ± 0.62 |
| Adriamycin-treated | 89.13 ± 12.57 |
| Adriamycin + F351-treated | 54.32 ± 10.88 |

Example 8

I. Treatment of Bleomycin-Induced Lung Fibrosis Using F351

Methods:

Forty eight (48) C57B6 mice (with body weight 16-18 g), half male and half female, were used in the study. Animals were divided into four groups with 12 animals per group. All the animals (except for those in control group) were injected with 5 mg/kg Bleomycin in the volume of 50 ul by intratracheal instillation on day 1 of the study. Animals in control group were injected by PBS instead. Details of the drug administration are described in Table 8.

TABLE 8

DRUG ADMINISTRATION IN THE STUDY

| Group | Administration |
|---|---|
| Control | Administered by gauvage, 0.5% CMC-Na, 0.2 ml/day for 28 days |
| Bleomycin-treated | Bleomycin was administered at 5 mg/kg in the volume of 50 ul by intratracheal instillation on day 1 |
| Bleomycin + dexamethasone-treated | Bleomycin was administered at 5 mg/kg in the volume of 50 ul by intratracheal instillation on day 1; dexamethasone by gauvage at 3 mg/kg per day in the volume of 0.2 ml for 28 days (dose was adjusted according to the animal's response) |
| Bleomycin + F351-treated | Bleomycin was administered at 5 mg/kg in the volume of 50 ul by intratracheal instillation on day 1; F351 by gauvage at 100 mg/kg/day in the volume of 0.2 ml for 28 days |

Results:

Pathology examination was performed at day 28. Animals in control group showed basically normal fibrotic tissues with slight thickness of alveolar wall, hyperplasia of pulmonary interstitial, and effusion of inflammatory cells. Fibrous tissue of animal in control group was basically normal. Animals in Bleomycin-treated group showed severe alveolar inflammation and hyperplasia of fibrotic tissue, thickness of alveolar wall, significant pulmonary interstitial hyperplasia, and an increased amount of effused inflammatory cells. Animals in Bleomycin+F351-treated group showed a significant improvement of the above pathological changes with reduced fibrosis. Animals in Bleomycin+Dex-treated group showed a slight improvement of the above pathological changes (FIG. 2).

Table 9 shows effects of F351 treatment on reduction of lung index. Lung index of animals in Bleomycin-treated group was significantly increased compared to those in control group. Lung index of animals in Bleomycin+F351-treated group was decreased compared to those in Bleomycin-treated group.

TABLE 9

EFFECT OF F351 TREATMENT ON REDUCTION OF LUNG INDEX

| Group | Lung Index (±S) |
| --- | --- |
| Control | 807.12 ± 100.60 |
| Bleomycin-treated | 2033.00 ± 1176.01 |
| Bleomycin + F351 (100 mg/kg)-treated | 1511.71 ± 945.55 |
| Bleomycin + dexamethasone-treated | 1083.90 ± 289.66 |

Example 9

I. Prevention and/or Treatment of Radiation-Induced Lung Fibrosis

Methods:

BalB/C male mice were randomly divided into three groups, namely, Control group (C group), Radiation group (R group), and Pirfenidone+Radiation (P+R group). All the animals were given single dose radiation on chest at 1200 cGy. Drugs were administrated two days before radiation for 12 weeks at 200 mg/kg/day. Examination includes cytometry of macrophages (performed 4 weeks and 8 weeks after drug administration), determination of hydroproline level (performed 16 weeks and 24 weeks after drug administration), and pathology examination of lung tissues by HE staining and Masson staining and evaluation of lung fibrosis by Ashcroft semi-quantitative evaluation standard under a microscope (performed 16 weeks and 24 weeks after drug administration).

Results:

Pirfenidone treatment had little toxic effect on BalB/C mice and reduced lung fibrosis mainly by decreasing congregation of macrophages in alveolus and collagen deposition in the lung. The study indicates that pirfenidone has preventive effects on radiation-induced lung fibrosis (Table 10).

TABLE 10

EFFECTS OF PIRFENIDONE ON PREVENTION AND/OR TREATMENT OF RADIATION-INDUCED LUNG FIBROSIS

A. Cytometry of macrophages ($1 \times 10^4$/ml)

| Group | 4 weeks | 8 weeks |
| --- | --- | --- |
| C group | 1.25 ± 1.37 | 1.09 ± 1.04 |
| R group | 9.17 ± 4.08 | 5.16 ± 2.16 |
| P + R group | 6.67 ± 2.04 | 2.27 ± 1.41 |
| P | 0.333 | 0.008 |

B. Evaluation on lung fibrosis

| Group | 16 weeks | 24 weeks |
| --- | --- | --- |
| C group | 11.55 ± 3.72 | 25.56 ± 15.17 |
| R group | 47.91 ± 22.49 | 42.50 ± 17.24 |
| P + R group | 29.15 ± 18.74 | 19.46 ± 6.67 |
| P | 0.039 | 0.000 |

C. Hydroproline level (μg/mg)

| Group | 16 weeks | 24 weeks |
| --- | --- | --- |
| C group | 62.30 ± 13.92 | 80.91 ± 19.68 |
| R group | 86.05 ± 11.92 | 104.14 ± 20.99 |
| P + R group | 67.65 ± 11.99 | 79.15 ± 10.90 |
| P | 0.007 | 0.001 |

Example 10

I. Prophylactic and/or Therapeutic Use of F351 in Drug-Induced Nephrotoxicity 1. Introduction—Kidney Fibrosis Kidney fibrosis, characterized by glomerulo-sclerosis and tubulointerstitial fibrosis, is a pathological manifestation of chronic kidney injury. Common insults inducing kidney fibrosis include chronic infection, obstruction of the ureter by calculi, malignant hypertension, severe diabetic conditions, and chronic exposure to heavy metals such as lead, vanadium, and mercury, or drugs such as diuretic, non-steroidal anti-inflammatory drug (NSAID), immunosuppressants, anti-tumor drugs and anticoagulants. In addition, idiopathic glomerulosclerosis and renal interstitial fibrosis have been reported in children and adults. Kidney fibrosis correlates well with the overall loss of renal function and frequently contributes to end-stage life-threatening renal failure.

2. Introduction—Drug-Induced Nephrotoxicity

Cyclosporine A (CsA), a calcineurin inhibitor, has improved allograft survival in solid organ transplantation and has been increasingly applied in the treatment of various autoimmune diseases. While marked progresses have been made in patients and allograft survival rates, clinical use of CsA is often limited by its nephrotoxic effects, which can be presented as two distinct and well-characterized forms: acute and chronic nephrotoxicity. The acute form is characterized by renal vasoconstriction, induced by an imbalance of vasoactive substances release, which leads to renal dysfunction. This form is reversible. The chronic toxicity, in contrast, is characterized by the vasoconstriction plus the development of structural damage that includes arteriolopathy and tubulointerstitial fibrosis that are often not reversible. The exact mechanisms of CsA-induced nephrotoxicity are not fully understood and there is no effective prevention or treatment for CsA-induced renal toxicity so far.

Adriamycin, a potent chemotherapeutic agent, is effective in treatment of leukemias, lymphomas and of many solid tumors. However, its clinical usage is often limited by toxic effects in many organs, including cardio toxicity, which is induced by oxygen radical damage of membrane lipids. In addition, Adriamycin causes severe nephrotoxicity in a variety of experimental animals, which represents a model very close to human progressive chronic renal disease. The molecular mechanism by which Adriamycin causes renal damage is unknown.

II. Treatment of Cyclosporine A-Induced Nephrotoxicity Using F351

Methods:

24 male Wistar rats (with body weight 180-220 g) were given low salt diet for 7 days before the study and randomly divided into three groups with 8 rats per group. The groups were named as control group, cyclosporine A (CsA)-treated group, and CsA+F351-treated group. The study was performed as shown in Table 11.

TABLE 11

DRUG ADMINISTRATION IN THE STUDY

| Group | Drug Administration |
| --- | --- |
| Control | Subcutaneous injection of olive oil |
| CsA-treated | Subcutaneous injection of 15 mg/kg CsA dissolved in olive oil |
| CsA + F351-treated | Subcutaneous injection of 15 mg/kg CsA dissolved in olive oil; F351 administered at 100 mg/Kg/day |

The animals were treated once a day for 28 days as indicated in the above table. Once every 7 days, the animals were weighed and the dose of CsA and F351 were adjusted in terms of body weight. Low salt diet was given to the animals during the whole study period.

Observation:

Mean arterial pressure was determined in alert state of the animals at the end of the study. Renal tissues were also collected for pathology examination.

Results:

As showed in Table 12, treatment of F351 reduced the mean tail arterial pressure and the degree of kidney fibrosis significantly.

TABLE 12

EFFECT OF F351 TREATMENT ON CsA-INDUCED NEPHROTOXICITY

| Group | Animal No. | Mean Arterial Pressure (kPa, x ± s) | Score on Kidney Fibrosis |
| --- | --- | --- | --- |
| Control | 8 | 15.66 ± 0.38 | 0.18 ± 0.04 |
| CsA-treated | 7 | 17.74 ± 0.51 | 1.13 ± 0.31 |
| CsA + F351-treated | 8 | 16.02 ± 0.27 | 0.62 ± 0.15 |

Figure 3A:
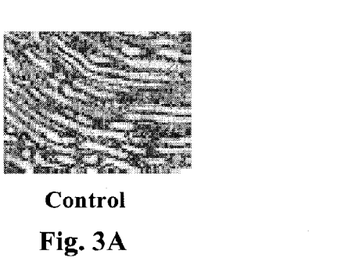
FIG. 3 shows effects of F351 on reduction of kidney fibrosis induced by cyclosporine A (CsA) via pathological examination with Masson Staining. Panel A: Control; Panel B: CsA-treated; and Panel C: CsA+F351-treated.
Figure 3B:
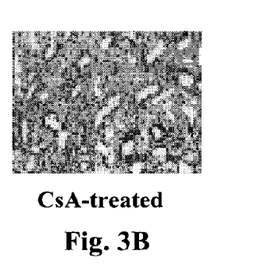
Figure 3C:
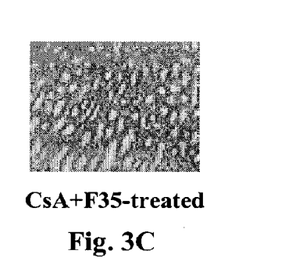

Pathology examination showed animals in CsA-treated group had various degrees of pathological changes, including tubulointerstitial fibrosis, tubular atrophy in the fibrotic area, and thickness of basal lamina. Kidney fibrosis in F351-treated animals was greatly reduced compared to animals in modeling group (FIG. 3).

III. Treatment of Adriamycin-Induced Nephrotoxicity

Methods:

20 male Wistar rats (with body weight 180-220 g) were randomly divided into three groups with 4 rats in control group, 8 rats in Adriamycin-treated group, and 8 rats in Adriamycin+F351-treated group. All the animals (except for those in control group) were injected with 7.5 mg/kg adriamycin by tail vein injection at day 1 of the study. Animals in control group were injected with PBS instead. Animals in Adriamycin+F351-treated group were administrated by gauvage with 250 mg/kg F351 per day for 12 weeks starting on day 1.

Observation:

Rat urine was collected 24 hours before the end of the study and amount of urine proteins was determined. Renal tissues were also collected for pathology examination.

Figure 4A:
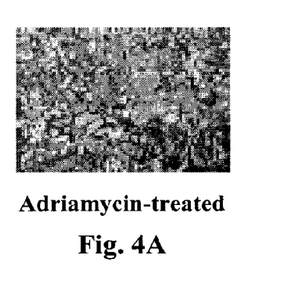
FIG. 4 shows effects of F351 on reduction of kidney fibrosis induced by Adriamycin via pathological examination with Masson Staining. Panel A: Adriamycin-treated; and Panel B: Adriamycin+F351-treated.
Figure 4B:
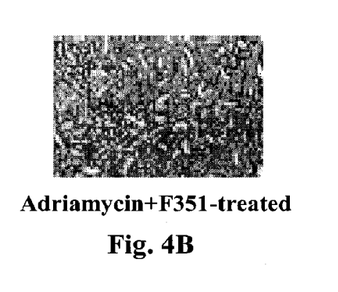

Results:

As shown in Table 13, treatment of F351 reduced amount of urine proteins significantly. It was also observed that treatment of F351 reduced the degree of kidney fibrosis by pathology examination. As shown in FIG. 4, animals in Adriamycin-treated group showed glomerular intumescence, increased mesangial cell proliferation and mesangial matrix, focal segmental sclerosis, hyperplasia of focal fibrous tissue in tubule, and increased collagen deposition (Green color in masson staining indicated collagen deposition). Animals in F351-treated group showed slight glomerular intumescence, normal mesangial cell proliferation, slight hyperplasia of focal fibrous tissue, decreased inflammatory cell infiltration, and reduced collagen deposition.

TABLE 13

EFFECT OF F351 ON REDUCTION OF AMOUNT OF URINE PROTEINS

| Group | Amount of Urine Proteins (mg/24 hrs, x ± s) |
| --- | --- |
| Control | 9.33 ± 0.62 |
| Adriamycin-treated | 89.13 ± 12.57 |
| Adriamycin + F351-treated | 54.32 ± 10.88 |

Example 11

I. Side Effects of Dexamethasone Compared with Pirfenidone

1. Introduction

Dexamethasone, a member of glucocorticoid hormones, has an effect on anti-inflammation and immune-suppression. The mechanism of action might involve inhibition of inflammatory cell infiltration, reduction of immune complex, inhibition of macrophage proliferation, and reduction of cytokine secretion by macrophage. Clinical use of dexamethasone is limited by its side effects, including depression, hypertension, nausea, acne, bone pain, muscle wasting, and anorexia. The side effects of dexamethasone also include risks of developing infection since dexamethasone suppresses the inflammatory response and makes it more difficult for a patient's body to fight off any infection.

2. Pharmacological Assay

Figure 5:
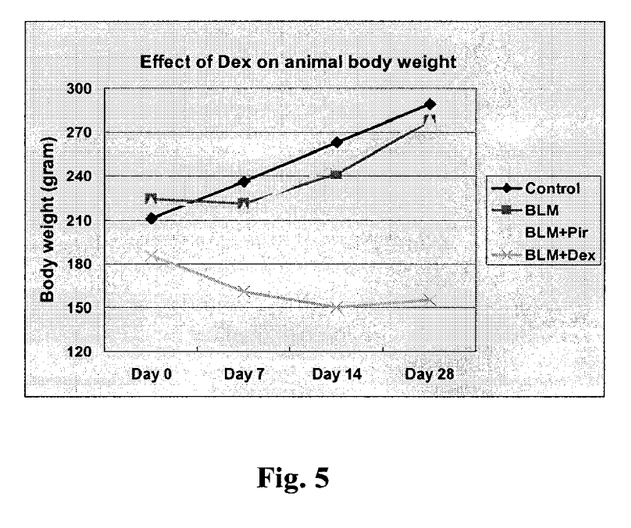
FIG. 5 is a graph showing adverse effects of dexamethasone on the weight of rats as compared with rats treated with pirfenidone.

Dexamethasone treatment was used as positive control in one study was designed to investigate the effects of pirfenidone on bleomycin-induced lung fibrosis in rat. Loss of body weight and high mortality rate were observed in dexamethasone-treated group (FIG. 5 and Table 14), though pathological examination showed dexamethasone treatment reduced lung fibrosis significantly. Further examination revealed that animal death was caused by toxicity effect induced by high dose of dexamethasone, rather than pulmonary alveolitis or pulmonary interstitial fibrosis.

TABLE 14

HIGH MORTALITY RATE OBSERVED IN
DEXAMETHASONE-TREATED GROUP

| Group | Number of dead animal | Mortality rate | P value |
|---|---|---|---|
| Control | 1/10 | 10% | 0.025 |
| Bleomycin-treated | 4/12 | 33.3% | 0.005 |
| Bleomycin + Pirfenidone-treated | 0/10 | 0% | |
| Bleomycin + Dexamethasone-treated | 9/14 | 64.3% | |

All references mentioned in this application are herein incorporated by reference into the specification to the same extent as if each was specifically and individually indicated to be incorporated herein by reference. Additionally, it will be understood that in light of the above disclosure of the present invention, those skilled in the art can make various changes and modifications, all of which are falling in the scope of the claims of the present invention.

What is claimed is:

1. A method for treating pneumonitis associated with a cytotoxic agent, an immunosuppressant, and/or radiation therapy in a mammal in need thereof comprising administering to the mammal a therapeutically effective amount of a compound of Formula I or a pharmaceutically acceptable salt thereof, (I)

wherein
$R_1$ is methyl, ethyl or trifluoromethyl at position 3, 4, 5 or 6; and
$R_2$ is hydroxyl, sulfydryl, $C_{1-6}$ alkoxyl such as methoxyl and ethoxyl, or a $C_{1-6}$ alkylthio group such as a methylthio group or an ethylthio group at position 2, 3 or 4; or, $R_2$ is absent.

2. The method of claim 1, wherein the compound of Formula I is pirfenidone.

* * * * *